(12) United States Patent
Choi et al.

(10) Patent No.: US 8,309,110 B2
(45) Date of Patent: Nov. 13, 2012

(54) BIOCIDE COMPOSITION AND STERILIZATION METHOD USING THE SAME

(75) Inventors: Ki-Seung Choi, Uiwang (KR); Jin-Man Kim, Suwon (KR); Jeong-Ho Park, Suwon (KR); Myung-Ho Cho, Suwon (KR); Soon-Jong Hahn, Seoul (KR)

(73) Assignee: SK Chemicals Co., Ltd., Kyungki-do (KR)

( * ) Notice: Subject to any disclaimer, the term of this patent is extended or adjusted under 35 U.S.C. 154(b) by 1920 days.

(21) Appl. No.: 10/933,189

(22) Filed: Sep. 2, 2004

(65) Prior Publication Data

US 2005/0101648 A1    May 12, 2005

Related U.S. Application Data

(63) Continuation-in-part of application No. 09/831,929, filed as application No. PCT/KR99/00687 on Nov. 16, 1999, now abandoned.

(30) Foreign Application Priority Data

Nov. 16, 1998   (KR) .................................. 1998-49095

(51) Int. Cl.
*A01N 25/00*   (2006.01)
*A61K 31/425*   (2006.01)
*A61K 31/155*   (2006.01)
(52) U.S. Cl. .......................... 424/405; 514/372; 514/634
(58) Field of Classification Search .................. 424/405; 514/372, 634
See application file for complete search history.

(56) References Cited

U.S. PATENT DOCUMENTS

| | | | |
|---|---|---|---|
| 3,761,488 A | 9/1973 | Lewis et al. | |
| 4,105,431 A | 8/1978 | Lewis et al. | |
| 4,279,762 A | 7/1981 | Lewis et al. | |
| 4,379,137 A | 4/1983 | Ehlers et al. | |
| 4,906,651 A * | 3/1990 | Hsu | 514/372 |
| 6,399,827 B1 | 6/2002 | Hahn et al. | |
| 2002/0065251 A1 | 5/2002 | Hahn et al. | |

FOREIGN PATENT DOCUMENTS

| | | |
|---|---|---|
| EP | 0773298 | 5/1997 |
| JP | 10175809 | 6/1998 |
| KR | 99025064 | 3/1999 |
| KR | 99059956 | 7/1999 |
| RU | 2057796 C1 * | 4/1996 |

OTHER PUBLICATIONS

American Type Culture Collection "*Bacillus subtilis* ATCC 6984" [retrieved on Oct. 18, 2003] Retrieved from the Internet: <URL: http://www.atcc.org/SearchCatalogs/Bacteria.cfm>.

American Type Culture Collection "*Enterobacter aerogenes* ATCC 13048" [retrieved on Oct. 18, 2003] Retrieved from the Internet: <URL: http://www.atcc.org/SearchCatalogs/Bacteria.cfm>.
American Type Culture Collection "*Escherichia coli* ATCC 11229" [retrieved on Oct. 18, 2003].
American Type Culture Collection, "*Micrococcus luteus* ATCC 9341" [retrieved on Oct. 18, 2003] Retrieved from the Internet: <URL: http://www.atcc.org/SearchCatalogs/Bacteria.cfm>.
American Type Culture Collection, "*Pseudomonas aeruginosa* ATCC 15442" [retrieved on Oct. 18 2003] Retrieved from the Internet: <URL: http://www.atcc.org/SearchCatalogs/Bacteria.cfm>.
American Type Culture Collection, "*Staphylococcus aureus* ATCC 6538" [retrieved on Oct. 18, 2003] Retrieved from the Internet: <URL: http://www.atcc.org/SearchCatalogs/Bacteria.cfm>.
American Type Culture Collection, "*Staphylococcus epidermis* ATCC 155" [retrieved on Oct. 18, 2003] Retrieved from the Internet: <URL: http://www.atcc.org/SearchCatalogs/Bacteria.cfm>.
Laopaiboon L et al., 2002, "The effect of a quaternary ammonium biocide on the performance and characteristics of laboratory-scale rotating biological contactors" J Appl Microbiol 93(6):1051-1058.
Kull FC et al, 1961, "Mixtures of quaternary ammonium compounds and long-chain fatty acids as antifungal agents" *Appl. Microbiol.* 9:538-541.
American Type Culture Collection, "*Escherichia coli* ATCC 11229" [retrieved on Oct. 18, 2003] Retrieved from the Internet: <URL: http://www.atcc.org/SearchCatalogs/Bacteria.cfm>.
American Type Culture Collection, "*Klebsiella pneumoniae* ATCC 4352" [retrieved on Jan. 9, 2009] Retrieved from the Internet: <URL: http://www.atcc.org/ATCCAdvancedCatalogSearch/ProductDetails/tabid/452/Default.aspx>.
American Type Culture Collection, "*Saccharomyces cerevisiae* ATCC 9763" [retrieved on Jan. 9, 2009] Retrieved from the Internet: <URL:http://www.atcc.org/ATCCAdvancedCatalogSearch/ProductDetails/tabid/452/Default.aspx>.
American Type Culture Collection, "*Rhizopus oryzae* ATCC 10404" [retrieved on Jan. 9, 2009] Retrieved from the Internet: <URL:http://www.atcc.org/ATCCAdvancedCatalogSearch/ProductDetails/tabid/452/Default.aspx>.
American Type Culture Collection, "*Aspergillus niger* ATCC 9642" [retrieved on Jan. 9, 2009] Retrieved from the Internet: <URL:http://www.atcc.org/ATCCAdvancedCatalogSearch/ProductDetails/tabid/452/Default.aspx>.

* cited by examiner

*Primary Examiner* — Aradhana Sasan
(74) *Attorney, Agent, or Firm* — Baker Botts, L.L.P.

(57) ABSTRACT

The present invention relates to antibacterial and antifungal compositions having 3-isothiazolone and polyhexamethyleneguanidine phosphate. These new antiseptic compositions demonstrate a superior degree of effectiveness on a wide spectrum of pathogens. The present invention also relates to the use of these new antiseptic compositions to kill and/or restrain the growth of bacteria and fungi in a variety of applications.

10 Claims, 1 Drawing Sheet

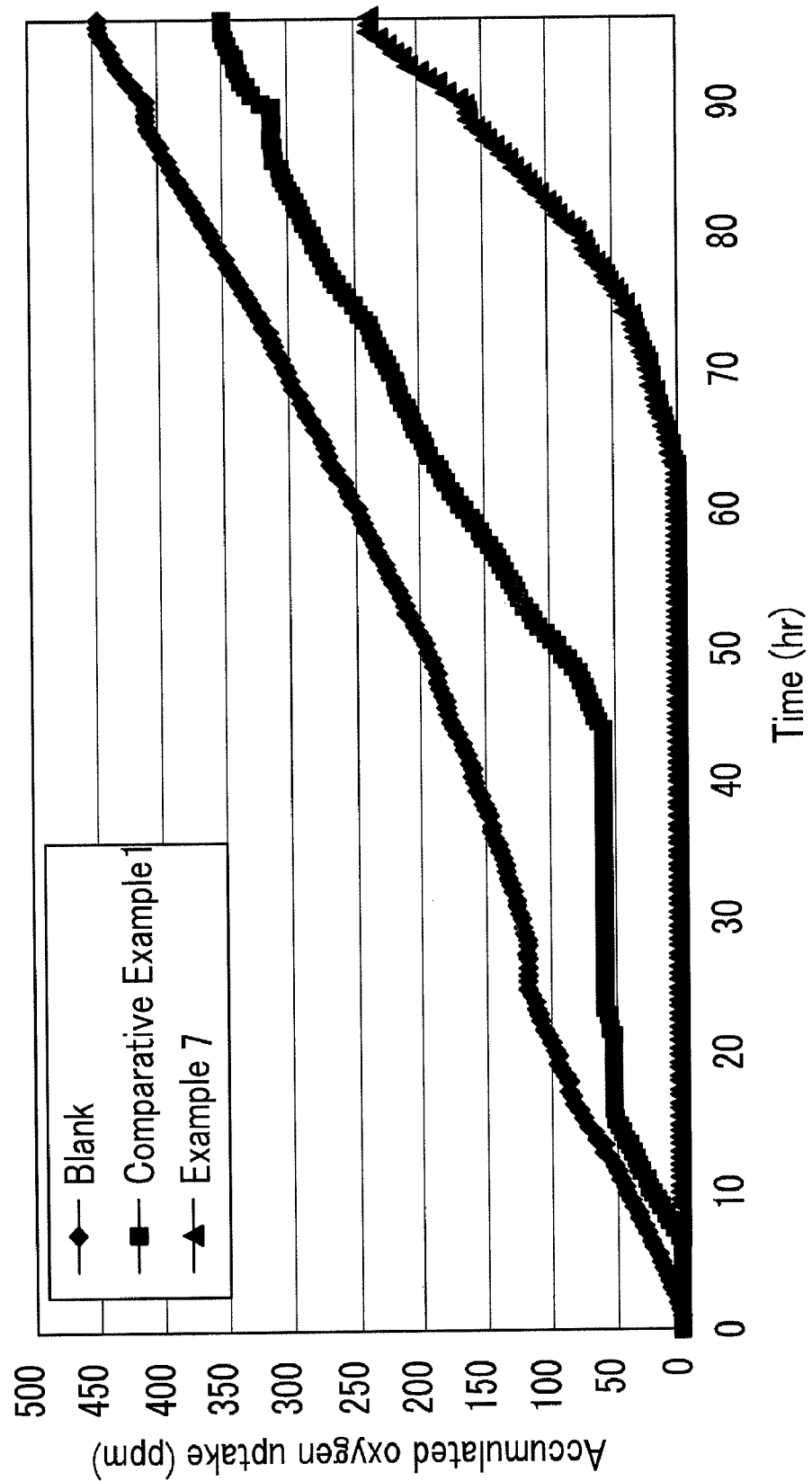

BIOCIDE COMPOSITION AND STERILIZATION METHOD USING THE SAME

This application is a continuation-in-part application of U.S. patent application Ser. No. 09/831,929, filed on Jun. 29, 2001, which is a 371 of PCT/KR99/00687, filed on Nov. 16, 1999, which claims the benefit of Republic of Korea 199849095, filed on Nov. 16, 1998, each of which is incorporated herein by reference in its entirety.

BACKGROUND OF THE INVENTION

1. Field of the Invention

The present invention relates to a biocide composition, more particularly to a biocide composition having synergistic effects by comprising 3-isothiazolone and polyhexamethyleneguanidine phosphate and a method for sterilizing microorganisms, fungi, etc. using the same.

2. Description of the Related Art

Microorganisms, bacteria, mold, algae, etc. grow in industrial water such as cooling water, wastewater, emulsifiers used in the textile industry, etc. and have a deteriorating effective on the operations of industrial processes. Such microorganisms propagate using organisms contained in the industrial water as a nutrient source and secrete polysaccharides. Varieties of organic and inorganic substances combined with these secreted polysaccharides and form viscous lumps or masses also called slime. Organic materials such as cellulose, hemicellulose, and the fibrin of white water in paper industry in particular provide to have sufficient nutrient sources for such microorganisms. The slime formed at areas of low fluid flow in a paper processing process results in both direct and indirect losses, such as manufacturing time loss, equipment efficiency deterioration, etc. due to the deterioration of pulp quality, etc. Furthermore, the growth of microorganisms at such places like a cooling water facility, where much water is contained or recirculated causes a fouling phenomena. This deteriorates heat transfer efficiency in an industrial cooling tower, as well as corrodes metal or erodes wooden parts.

Bacteria such as taloblastic prokaryotes can propagate by decomposing various types of organisms, some of which are the sources of the microbiologically induced corrosion, by secreting and discharging polysaccharides forming a biofilm. Fungi such as eukaryote can also propagate by decomposing various types of organisms like bacteria, and some types of fungi secreting cellulase are the sources for discoloration and decomposition of wooden parts by way of degrading the fibroid materials of wooden parts of a cooling tower, etc.

Algae, such as eukaryote, can propagate by photosynthesizing under an environment with light, air, and a small amount of organisms, and carbohydrate formed from algae is used as a nutrient source for other microorganisms such as bacteria and fungi, thereby accelerating the fouling phenomena. Algal fouling due to algae propagation is intensified at places that are exposed to sunlight, particularly in cooling water facilities, swimming pools, etc. This phenomena results in clogging which blocks water pipes, as well as the deterioration of heat transfer efficiency, oxidization of metal surfaces by the generation of oxygen, and the promotion of corrosion at a holes on metallic surfaces through a partial galvanic reaction when the organism dies.

Various biocides are being developed in order to kill such microorganisms, fungi, algae, etc. or to prevent their surface adhesion to metal, etc. These biocides are generally divided into oxidant biocides and non-oxidant biocides. The oxidant biocides that are mainly used are halogen compounds such as chlorine, bromine, etc. that are popular due to their economic advantage of strong oxidation capability and low price. However, they can cause erosion of the wooden parts of cooling towers and metallic decomposition, and their sterilizing efficiency tends to deteriorate as they can be easily being discharged into atmosphere. Furthermore, their practical effectiveness is poor due their peculiar way of first reacting with secreted polysaccharides before they react with microorganisms that are the actual sources of biofilm formation.

Non-oxidant biocides which overcome these disadvantages include 3-isothiazolone, quaternary ammonium salt, formaldehyde emission compound, glutaraldehyde, etc. and are mainly used separately. Although 3-isothiazolone, which is disclosed in U.S. Pat. Nos. 3,761,488, 4,105,431, 4,279,762, etc., has a high sterilizing effect and wide antibiotic spectrum, it has a disadvantage in that its immediate instantaneous sterilizing effects are low. Furthermore, Korean Patent Application No. 89-20381 discloses an antiseptic composition useful in preventing circulation water putrefaction wherein a biocides 5-chloro-2-methyl-4-isothiazolone-3-on and 2-methyl-4-isothiazolone-3-on are mixed in a ratio of about 3:1 and wherein this antiseptic composition further comprises didecyldimethylammoniumchloride. U.S. Pat. No. 4,379,137 discloses a method for improving sterilizing capability by mixing polymer quaternary ammonium salt and 3-isothiazolone. However, since these mixtures emit corrosive materials, i.e., halogen compounds such as fluorine, chlorine, etc., it is difficult for them to be applied where metals susceptible to corrosion are used, such as carbon steel, cast iron, stainless steel, copper, etc.

Additionally, Korean Patent Application No. 97-80170 discloses a process that can be applied even when metals susceptible to corrosion are used since the disclosed process does not emit a halogen compound. Another water soluble biocide composition having synergistic effects comprising 3-isothiazolone, which has high sterilizing effect on quartemary ammonium phosphate and microorganisms, is disclosed in Korean Patent Application No. 97-46517 as a biocide having superior properties of immediate sterilizing effects on microorganisms, durability, anticorrosiveness, etc. However, there is a problem in applying this invention to various industrial fields due to the issues such as bubbling or foaming, etc. when quaternary ammonium is added to provide immediate effectiveness to the 3-isothiazolone.

Furthermore, while polyhexamethyleneguanidine phosphate has immediate effectiveness, and is used in the effective and wide control of microorganisms in various industrial fields, including water treatment, as well as exhibiting low foaming properties, it has a disadvantage of not having a wide antibiotic spectrum by itself.

SUMMARY OF THE INVENTION

It is an object of the present invention to provide a biocide composition which can be used in the process where metals susceptible to corrosion are used, such as carbon steel, cast iron, stainless steel, copper, etc., as well as which has high sterilizing capability, a wide antibiotic spectrum, and superior antiseptic effects.

It is an other object of the present invention to provide a biocide composition which can not only be applied to various industrial processes on account of its low foaming features, but also which has a high sterilizing capability even when a small amount is used.

The present invention provides a biocide composition comprising 3-isothiazolone of the following General Formula 1 and polyhexamethyleneguanidine phosphate of the following General Formula 2 in order to accomplish the above objects:

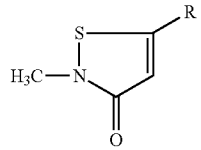

[General Formula 1]

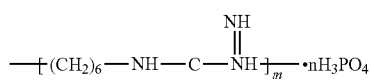

[General Formula 2]

where R is hydrogen or chlorine in the above General Formula 1 in the above General Formula 1, m is integer from 4 to 7, and n is an integer from 1 to 14 in the above General Formula 2. The present invention further provides a sterilizing method which kills or restrains the growth of bacteria, fungi or algae by inputting the above biocide composition into a media that is contaminated by bacteria, fungi, and algae.

BRIEF DESCRIPTION OF THE DRAWINGS

FIG. 1 depicts the accumulated oxygen uptake in cooling water of a polymerization cooling tower having a microorganism concentration of about 104 CFU/ml following the addition of (a) 100 ppm of a biocide mixture of 3-isothiazolone and polyhexamethyleneguanidine phosphate, (b) 1.5% 3-isothiazolone, or (c) a blank solution in which no biocide was added.

DETAILED DESCRIPTION OF THE PREFERRED EMBODIMENTS

In the following detailed description, only the preferred embodiments of the invention have been shown and described, simply by way of illustration of the best mode contemplated by the inventor(s) of carrying out the invention. As will be realized, the invention is capable of modification in various obvious respects, all without departing from the invention. Accordingly, the description is to be regarded as illustrative in nature, and not restrictive.

The present invention is described in detail below.

The present invention provides an antiseptic and/or biocide composition comprising 3-isothiazolone of the below General Formula 1 and polyhexamethyleneguanidine phosphate of the below General Formula 2:

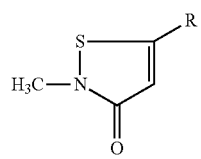

[General Formula 1]

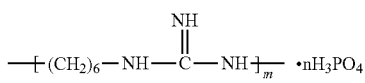

[General Formula 2]

where R is hydrogen or chlorine in the above General Formula 1 in the above General Formula 1, m is integer from 4 to 7, and n is an integer from 1 to 14 in the above General Formula 2.

In the above General Formulae, 3-isothiazolone is preferably 2-methyl-4-isothiazolone-3-on having R group of hydrogen or 5-chloro-2-methyl-4-isothiazolone-3-on having R group of chlorine, and more preferably a mixture in which 2-methyl-4-isothiazolone-3-on and 5-chloro-2-methyl-4-isothiazolone-3-on are mixed in a weight ratio of 1:20 to 20:1. If the above ratio of 3-isothiazolone compound is out of the range of 1:20 to 20:1, the sterilizing effects are deteriorated.

The mixing ratio of the above 3-isothiazolone and polyhexamethyleneguanidine phosphate is preferably a weight ratio of 1:1 to 1:65, more preferably 1:1 to 1:4. If the above mixing ratio of 3-isothiazolone and polyhexamethyleneguanidine phosphate is out of the above range, the synergistic effects by the mixture of two biocides are deteriorated or not seen.

If the present invention of a mixture of 3-isothiazolone and polyhexamethyleneguanidine phosphate are used as a biocide composition, 3-isothiazolone compensates for the disadvantage in the low sterilizing effects of polyhexamethyleneguanidine phosphate on fungi and some bacteria, while polyhexamethyleneguanidine phosphate compensates for the disadvantage of 3-isothiazolone has in its low initial and immediate sterilizing capability and effectiveness. Synergistic effects are seen in that the sterilizing action of a mixed biocide becomes greater than the sum of the sterilizing action that each component compound has. That is, the present invention of a composition can restrain microorganisms more widely and effectively by mixing the two types of compounds having different sterilizing mechanisms, and obtains further effects such as the lowering of an emergence frequency of resistant strains more than in the case of using a single component compound.

A biocide composition of the present invention is preferably used in an aqueous solution and more preferably used by putting 5 to 1,000 parts per million (ppm) of it into cooling water, etc. in which the microorganisms exist, although the amount used has no limit as long as it achieves the targeted sterilizing effects. A biocide composition of the present invention can be used in controlling microorganisms widely and effectively in the various industrial fields such as in pulp and paper plants, cooling towers, as a disinfectant, etc. In particular, it can be used by adding it to the cooling water of an industrial process, to disinfectant, paint, latex antiseptic, cosmetic additives, additives for emulsion products such as shampoo, etc., slime control chemicals for textile weaving, paper slime control agent, and antiseptics for leather goods, metal processing oil, etc.

COMPARATIVE EXAMPLES for helping in gaining in an understanding of the present invention and preferable EXAMPLES are described below.

EXAMPLES 1-6

The sterilizing effects of 3-isothiazolone and polyhexamethyleneguanidine phosphate on a mixed solution of 8 types of bacteria (*Enterobacter* aerogens ATCC 13048, *Escherichia coli* ATCC 11229, *Micrococcus luteus* ATCC 9341, *Pseudomonas aeruginosa* ATCC 15442, *Klebsiella pneumoniae*, *Staphylococcus epidermis* ATCC 155, *Staphylococcus aureus* ATCC 6538, and *Bacillus subtilis* ATCC 6984) were tested using Tryptic Soy Broth manufactured by Difco Corporation according to the two fold dilution method. The minimum inhibiting concentration of each biocide and mixtures thereof were determined by observation with the naked eye of the degree of muddiness of the lowest concentration in which growth was deteriorated after culturing a culture fluid in which biocides and microorganisms are added at 30 degrees centigrade for 3 days.

It was determined that a synergistic effect of a biocide was seen when the sum of QA/Qa and QB/Qb was less than 1, as in the following EQUATION according to the method published in the paper of Kull, F. C. et al (Appl. Microbiol. 9:53 8~544 (1961)), and these results are represented in Table 1:

Synergistic Index($SI$)=($QA/Qa$)+($QB/Qb$)

where Qa and Qb are MIC values (ppm) of a single compound A and single compound B, respectively, and QA and QB are MIC values (ppm) of the compounds A and B, respectively, out of each mixture.

TABLE 1

|  | Qa | Qb | QA | QB | QA/Qa | QB/Qb | SI |
|---|---|---|---|---|---|---|---|
| EXAMPLE 1 | 18.8 | 312.5 | 9.4 | 9.8 | 0.5 | 0.03 | 0.53 |
| EXAMPLE 2 | 18.8 | 312.5 | 9.4 | 19.5 | 0.5 | 0.06 | 0.56 |
| EXAMPLE 3 | 18.8 | 312.5 | 9.4 | 39.1 | 0.5 | 0.13 | 0.63 |
| EXAMPLE 4 | 18.8 | 312.5 | 9.4 | 78.1 | 0.5 | 0.25 | 0.75 |
| EXAMPLE 5 | 18.8 | 312.5 | 9.4 | 156.3 | 0.5 | 0.50 | 1.0 |
| EXAMPLE 6 | 18.8 | 312.5 | 2.4 | 156.3 | 0.13 | 0.50 | 0.63 |
| EXAMPLE 7 | 18.8 | 312.5 | 2.4 | 39.1 | 0.13 | 0.13 | 0.26 |

Qa: MIC value (ppm) on the mixed strain of a single 3-isothiazolone;
Qb: MIC value (ppm) on the mixed strain of a single polyhexamethyleneguanidine phosphate;
QA: MIC value (ppm) of 3-isothiazolone out of a mixture;
QB: MIC value (ppm) of polyhexamethyleneguanidine out of a mixture.

As represented in the above Table 1, it can be seen that the same microorganism killing effect (SI was 0.53 in EXAMPLE 1) can be obtained even though only a half amount of 3-isothiazolone is used and the amount of polyhexamethyleneguanidine phosphate used is reduced to 9.8 ppm. The same microorganism killing effect (SI was 0.63 in EXAMPLE 6) can also be obtained even though only a half amount of polyhexamethyleneguanidine phosphate is used and only 2.4 ppm of 3-isothiazolone is used, and the same microorganism killing effect (SI was 0.25 in EXAMPLE 7) can also be obtained even though only 39.1 ppm of polyhexamethyleneguanidine phosphate and 2.4 ppm of 3-isothiazolone are used. Therefore, it can be shown that a mixture of the above two compounds can inhibit the growth of bacteria more effectively than the single use of each of the two compounds, and the synergistic action ratio of 3-isothiazolone and polyhexamethyleneguanidine phosphate is most preferable in the range of 1:1 to 1:16, where SI is from 0.26 to 0.63.

Test Example 1 and Comparative Example 1

The minimum inhibition concentration (MIC) values of a biocide composition in which 3-isothiazolone and polyhexamethyleneguanidine phosphate are mixed in a ratio of 1:4 (1 wt % of 3-isothiazolone and 15 wt % of 25 wt % polyhexamethyleneguanidine phosphate) and of a single biocide of 1.5 wt % 3-isothiazolone were measured on 7 types of individual strains. After diluting a biocide using 96 multi wall plates according to the two fold continuous dilution method, microorganisms were inoculated at a concentration of 104 CFU/ml. Then, after culturing at 30 degrees centigrade for 48 hours, the MIC values were measured by observation with the naked eye of the growth of microorganisms on the basis of muddiness. The results are represented in Table 2.

The muddiness was observed using Tryptic Soy Broth manufactured by Difco Corporation as a medium in order to measure MIC values and strains of *Enterobacter* aerogens ATCC 13048, *Staphylococcus aureus* ATCC 6538, *Staphylococcus epidermis* ATCC 155, *Bacillus subtilis* ATCC 6984, *Saccharomyces cerevisiae* ATCC 9763, *Rhizopus oryzae* ATCC 10404, *Aspergillus niger* ATCC 9642 were used from among the strains which were used in EXAMPLE 1.

TABLE 2

MIC test results on microorganisms of a biocide mixture and a single biocide of 1.5 wt % 3-isothiazolone (units: ppm):

| Strains Used | COMPARATIVE EXAMPLE (1.5% isothiazolone) | TEST EXAMPLE (Biocide mixture) |
|---|---|---|
| *Enterobacter aerogens* ATCC 13048 | 390 | 195 |
| *Staphylococcus aureus* ATCC 6538 | 195 | 195 |
| *Staphylococcus epidermis* ATCC 155 | 390 | 97 |
| *Bacillus subtilis* ATCC 6984 | 390 | 195 |
| *Saccharomyces cerevisiae* ATCC 9763 | 390 | 390 |
| *Rhizopus oryzae* ATCC 10404 | 390 | 195 |
| *Aspergillus niger* ATCC 9642 | 195 | 195 |

As can be shown from the above Table 2, a biocide mixture in which 3-isothiazolone and 25 wt % polyhexamethyleneguanidine phosphate are mixed using the synergistic index is much more effective in controlling microorganisms than is a biocide with a single component of 1.5 wt % 3-isothiazolone.

Test Example 2 and Comparative Example 2

In order to determine the killing time to kill microorganisms when the biocide mixture used in TEST EXAMPLE 1 and 1.5% 3-isothiazolone that was used in COMPARATIVE EXAMPLE 1, measurements were made of the immediate effectiveness, the durability, and the number of strains by taking a strain solution at times corresponding to 0 hours, 3 hours, 24 hours, 48 hours, 72 hours, and 96 hours after respectively putting in 50, 100, and 200 ppm of a biocide mixture and 1.5% 3-isothiazolone into the cooling water of a polymerization cooling tower having a microorganism concentration of about 104 CFU/ml. A solution in which a biocide was not added was used as a blank. The measured results on the strain reduction ratios according to the time when the biocide mixture in which 3-isothiazolone and polyhexamethyleneguanidine phosphate was mixed are presented using a synergistic index, as well as data for single component biocide of 1.5 wt % 3-isothiazolone, are represented in Table 3 and Table 4.

TABLE 3

Measured results on the reduction ratio of microorganisms according to the concentration of a biocide mixture verses time (units: CFU/ml):

|  |  | 0 | 3 hours | 24 hours | 48 hours | 72 hours | 96 hours |
|---|---|---|---|---|---|---|---|
|  | Blank | 13,000 | >13,000 | >13,000 | >13,000 | >13,000 | >13,000 |
| Biocide | 50 ppm | 13,000 | 210 | 140 | 90 | 40 | 50 |
| mixture | 100 ppm | 13,000 | 80 | 170 | 90 | 50 | 30 |
|  | 200 ppm | 13,000 | 50 | 90 | 50 | 40 | 50 |

TABLE 4

Measured results on the reduction ratio of microorganisms according to the concentration verses time of 1.5 wt % of 3-isothiazolone (units: CFU/ml):

|  |  | 0 | 3 hours | 24 hours | 48 hours | 72 hours | 96 hours |
|---|---|---|---|---|---|---|---|
|  | Blank | 13,000 | >13,000 | >13,000 | >13,000 | >13,000 | >13,000 |
| 1.5 wt % of | 50 ppm | 13,000 | 12,000 | 450 | >10,000 | >10,000 | >10,000 |
| isothiazolone | 100 ppm | 13,000 | 11,400 | 370 | 6,250 | >10,000 | >10,000 |
|  | 200 ppm | 13,000 | 5,300 | 200 | 2,100 | >10,000 | >10,000 |

As can be shown in the above Table 3 and Table 4, the single compound 1.5 wt % of 3-isothiazolone biocide shows sterilizing capability after 24 hours, while the immediate effectiveness is low and there is also a secondary propagation of microorganisms after 48 hours. The biocide mixture of 3-isothiazolone and polyhexamethyleneguanidine phosphate achieves synergistic effects as seen in immediate effectiveness, durability, and superior sterilizing effects on microorganisms as compared to the single component biocide. Therefore, it can be shown that when 3-isothiazolone and polyhexamethyleneguanidine phosphate are mixed, the disadvantage of 3-isothiazolone with immediate effectiveness and the problems of polyhexamethyleneguanidine phosphate associated with antibiotic spectrum are mutually compensated, and sterilizing capability is correlated with a synergistic effect index.

Test Example 3 and Comparative Example 3

In order to determine the killing time of microorganisms when the biocide mixture used in EXAMPLE 7 and 1.5% 3-isothiazolone that was used in COMPARATIVE EXAMPLE 1 are used, measurements were made of the immediate effectiveness, the durability, and the growth of microorganisms using a respirometer after respectively putting 100 ppm of a biocide mixture and 1.5% 3-isothiazolone into the cooling water of a polymerization cooling tower having a microorganism concentration of about 104 CFU/ml. A solution in which a biocide was not added was used as a blank. The measured results on the strain reduction ratios according to time when the biocide mixture in which 3-isothiazolone and polyhexamethyleneguanidine phosphate were mixed are presented using a synergistic index, as well as data for a single component biocide of 1.5 wt % 3-isothiazolone, are represented in Table 5 and FIG. 1.

TABLE 5

(Unit: ppm)

| Time (hr) | Blank | Comparative Example 1: Oxygen Consumption Rate | Example 7: Oxygen Consumption Rate |
|---|---|---|---|
| 0 | 0 | 0 | 0 |
| 0.5 | 0 | 0 | 0 |
| 1 | 0 | 0 | 0 |
| 1.5 | 3.1 | 0 | 0 |
| 2 | 4.2 | 0 | 0 |
| 2.5 | 6.2 | 0 | 0 |
| 3 | 8.3 | 0 | 0 |
| 3.5 | 10.4 | 0 | 0 |
| 4 | 12.4 | 0 | 0 |
| 4.5 | 14.5 | 0 | 0 |
| 5 | 17.6 | 0 | 0 |
| 5.5 | 19.7 | 0 | 0 |
| 6 | 21.8 | 0 | 0 |
| 6.5 | 24.9 | 0 | 0 |
| 7 | 27 | 2 | 0 |
| 7.5 | 29.1 | 6.1 | 0 |
| 8 | 32.2 | 10.2 | 0 |
| 8.5 | 34.2 | 12.3 | 0 |
| 9 | 37.4 | 16.3 | 0 |
| 9.5 | 39.4 | 19.4 | 0 |
| 10 | 42.6 | 22.4 | 0 |
| 10.5 | 44.6 | 25.5 | 0 |
| 11 | 47.7 | 27.6 | 0 |
| 11.5 | 49.8 | 30.6 | 0 |
| 12 | 52.9 | 33.7 | 0 |
| 12.5 | 56 | 35.7 | 0 |
| 13 | 59.2 | 37.7 | 0 |
| 13.5 | 61.2 | 38.8 | 0 |
| 14 | 66.4 | 42.8 | 0 |
| 14.5 | 69.5 | 44.9 | 0 |
| 15 | 72.6 | 47.9 | 0 |
| 15.5 | 75.8 | 50 | 0 |
| 16 | 78.9 | 51 | 0 |
| 16.5 | 82 | 52 | 0 |
| 17 | 84.1 | 52 | 0 |
| 17.5 | 87.2 | 52 | 0 |
| 18 | 87.2 | 52 | 0 |
| 18.5 | 89.2 | 52 | 0 |
| 19 | 92.4 | 52 | 0 |
| 19.5 | 94.4 | 52 | 0 |
| 20 | 95.5 | 52 | 0 |
| 20.5 | 96.5 | 52 | 0 |
| 21 | 99.6 | 52 | 0 |
| 21.5 | 102.8 | 52 | 0 |
| 22 | 104.8 | 53.1 | 0 |

TABLE 5-continued

| Time (hr) | Blank | Comparative Example 1: Oxygen Consumption Rate | Example 7: Oxygen Consumption Rate (Unit: ppm) |
|---|---|---|---|
| 22.5 | 106.9 | 54 | 0 |
| 23 | 109 | 55.1 | 0 |
| 23.5 | 111 | 57.1 | 0 |
| 24 | 112.1 | 57.1 | 0 |
| 24.5 | 116.2 | 58.1 | 0 |
| 25 | 117.3 | 58.1 | 0 |
| 25.5 | 117.3 | 58.1 | 0 |
| 26 | 117.3 | 58.1 | 0 |
| 26.5 | 117.3 | 58.1 | 0 |
| 27 | 117.3 | 58.1 | 0 |
| 27.5 | 117.3 | 58.1 | 0 |
| 28 | 117.3 | 58.1 | 0 |
| 28.5 | 118.3 | 58.1 | 0 |
| 29 | 120.4 | 58.1 | 0 |
| 29.5 | 121.4 | 58.1 | 0 |
| 30 | 122.5 | 58.1 | 0 |
| 30.5 | 124.5 | 58.1 | 0 |
| 31 | 125.6 | 58.1 | 0 |
| 31.5 | 126.6 | 58.1 | 0 |
| 32 | 128.7 | 58.1 | 0 |
| 32.5 | 130.8 | 58.1 | 0 |
| 33 | 131.8 | 58.1 | 0 |
| 33.5 | 133.9 | 58.1 | 0 |
| 34 | 134.9 | 58.1 | 0 |
| 34.5 | 137 | 58.1 | 0 |
| 35 | 138 | 58.1 | 0 |
| 35.5 | 140.1 | 58.1 | 0 |
| 36 | 142.2 | 58.1 | 0 |
| 36.5 | 144.3 | 58.1 | 0 |
| 37 | 145.3 | 58.1 | 0 |
| 37.5 | 147.4 | 58.1 | 0 |
| 38 | 149.4 | 58.1 | 0 |
| 38.5 | 151.5 | 58.1 | 0 |
| 39 | 152.5 | 58.1 | 0 |
| 39.5 | 154.6 | 58.1 | 0 |
| 40 | 156.7 | 58.1 | 0 |
| 40.5 | 158.8 | 58.1 | 0 |
| 41 | 159.8 | 58.1 | 0 |
| 41.5 | 161.9 | 58.1 | 0 |
| 42 | 164 | 58.1 | 0 |
| 42.5 | 166 | 58.1 | 0 |
| 43 | 168.1 | 58.1 | 0 |
| 43.5 | 170.2 | 58.1 | 0 |
| 44 | 173.3 | 58.1 | 0 |
| 44.5 | 175.4 | 62.2 | 0 |
| 45 | 177.5 | 64.3 | 0 |
| 45.5 | 179.6 | 66.3 | 0 |
| 46 | 180.6 | 68.4 | 0 |
| 46.5 | 182.7 | 70.4 | 0 |
| 47 | 183.7 | 72.4 | 0 |
| 47.5 | 185.8 | 74.5 | 0 |
| 48 | 186.8 | 77.5 | 0 |
| 48.5 | 188.9 | 81.6 | 0 |
| 49 | 190.9 | 85.7 | 0 |
| 49.5 | 193 | 89.8 | 0 |
| 50 | 195.1 | 93.9 | 0 |
| 50.5 | 197.2 | 97.9 | 0 |
| 51 | 200.3 | 102 | 0 |
| 51.5 | 202.4 | 107.1 | 0 |
| 52 | 205.5 | 111.2 | 0 |
| 52.5 | 208.6 | 114.2 | 0 |
| 53 | 210.7 | 118.3 | 0 |
| 53.5 | 213.8 | 121.4 | 0 |
| 54 | 215.9 | 124.4 | 0 |
| 54.5 | 219 | 126.5 | 0 |
| 55 | 221.1 | 129.5 | 0 |
| 55.5 | 224.2 | 132.6 | 0 |
| 56 | 226.2 | 135.7 | 0 |
| 56.5 | 229.3 | 138.7 | 0 |
| 57 | 231.4 | 141.8 | 0 |
| 57.5 | 233.5 | 144.8 | 0 |
| 58 | 236.6 | 148.9 | 0 |
| 58.5 | 239.7 | 152 | 0 |
| 59 | 241.8 | 156.1 | 0 |
| 59.5 | 243.9 | 159.1 | 0 |
| 60 | 247 | 163.2 | 0 |
| 60.5 | 250.1 | 167.3 | 0 |
| 61 | 252.2 | 170.3 | 0 |
| 61.5 | 255.3 | 173.4 | 0 |
| 62 | 257.4 | 177.5 | 0 |
| 62.5 | 260.5 | 180.5 | 0 |
| 63 | 263.6 | 183.6 | 2 |
| 63.5 | 266.7 | 187.7 | 4 |
| 64 | 268.8 | 190.8 | 6 |
| 64.5 | 271.9 | 192.8 | 7.1 |
| 65 | 274 | 195.8 | 8.1 |
| 65.5 | 276.1 | 197.9 | 9.1 |
| 66 | 279.2 | 201 | 11.1 |
| 66.5 | 282.3 | 203 | 13.1 |
| 67 | 285.4 | 205 | 14.1 |
| 67.5 | 287.5 | 208.1 | 16.1 |
| 68 | 289.6 | 211.1 | 17.2 |
| 68.5 | 292.7 | 213.2 | 18.1 |
| 69 | 295.8 | 215.2 | 20.2 |
| 69.5 | 297.9 | 216.3 | 21.2 |
| 70 | 299.9 | 219.3 | 22.2 |
| 70.5 | 303 | 222.4 | 23.2 |
| 71 | 305.1 | 224.4 | 25.2 |
| 71.5 | 308.2 | 227.5 | 27.2 |
| 72 | 311.4 | 229.5 | 28.2 |
| 72.5 | 313.4 | 231.6 | 30.2 |
| 73 | 315.5 | 233.6 | 32.3 |
| 73.5 | 318.6 | 236.6 | 34.3 |
| 74 | 320.7 | 240.7 | 36.3 |
| 74.5 | 323.8 | 244.8 | 39.3 |
| 75 | 327.9 | 248.9 | 42.3 |
| 75.5 | 331.1 | 253 | 45.4 |
| 76 | 334.2 | 257.1 | 48.4 |
| 76.5 | 337.3 | 261.1 | 52.4 |
| 77 | 340.4 | 264.2 | 55.5 |
| 77.5 | 343.5 | 267.3 | 58.5 |
| 78 | 346.6 | 269.3 | 62.5 |
| 78.5 | 348.7 | 272.4 | 65.5 |
| 79 | 351.8 | 274.4 | 69.6 |
| 79.5 | 354.9 | 277.4 | 73.6 |
| 80 | 358 | 279.5 | 77.6 |
| 80.5 | 361.2 | 282.6 | 81.7 |
| 81 | 364.3 | 285.6 | 86.7 |
| 81.5 | 367.4 | 287.6 | 90.8 |
| 82 | 370.5 | 290.7 | 94.8 |
| 82.5 | 373.6 | 292.8 | 99.8 |
| 83 | 376.7 | 294.8 | 104.9 |
| 83.5 | 379.8 | 297.9 | 109.9 |
| 84 | 382.9 | 299.9 | 113.9 |
| 84.5 | 386.1 | 302.9 | 119 |
| 85 | 389.2 | 305 | 124 |
| 85.5 | 392.3 | 308.1 | 129.1 |
| 86 | 395.4 | 309.1 | 134.1 |
| 86.5 | 398.5 | 310.1 | 139.1 |
| 87 | 400.6 | 311.1 | 144.2 |
| 87.5 | 403.7 | 311.1 | 149.2 |
| 88 | 406.8 | 311.1 | 154.3 |
| 88.5 | 408.9 | 311.1 | 159.3 |
| 89 | 408.9 | 311.1 | 160.3 |
| 89.5 | 408.9 | 311.1 | 162.3 |
| 90 | 408.9 | 319.3 | 168.4 |
| 90.5 | 414.1 | 325.4 | 176.4 |
| 91 | 419.3 | 329.5 | 183.5 |
| 91.5 | 423.4 | 333.6 | 191.6 |
| 92 | 426.6 | 335.6 | 197.6 |
| 92.5 | 430.7 | 337.6 | 205.7 |
| 93 | 433.8 | 338.7 | 210.7 |
| 93.5 | 435.9 | 341.7 | 215.8 |
| 94 | 438 | 343.7 | 221.8 |
| 94.5 | 442.1 | 346.8 | 228.9 |
| 95 | 445.2 | 347.8 | 235.9 |
| 95.5 | 446.3 | 347.8 | 235.9 |
| 96 | 446.3 | 347.8 | 235.9 |
| 96.5 | 446.3 | 347.8 | 235.9 |

In addition, the accumulated oxygen uptakes of the biocide mixture used in EXAMPLE 7 and 1.5% 3-isothiazolone that was used in COMPARATIVE EXAMPLE 1 were measured, and the results are presented in FIG. 1. As shown in FIG. 1, EXAMPLE 7 exhibits better accumulated oxygen uptakes than COMPARATIVE EXAMPLE 1.

As described in the above, a biocide composition of the present invention can be effectively used in the wide control of microorganisms in various industrial fields such as water treatment, disinfectants, etc., since it has immediate effectiveness and durability, as well as applicability to a wide antibiotic spectrum. Furthermore, a biocide composition of the present invention can effectively control industrial water microorganism contamination and the actual living environment of the microorganisms since it is more effective in controlling the microorganisms and has greater immediate sterilizing capability than does a single compound biocide. A biocide composition of the present invention has an effect to lower the emergence frequency of a resistant strain as compared a single compound biocide, achieving this using a mixture of biocides having the different working mechanism.

While the present invention has been described in detail with reference to the preferred embodiments, those skilled in the art will appreciate that various modifications and substitutions can be made thereto without departing from the spirit and scope of the present invention as set forth in the appended claims. All publications and patents cited above are herein incorporated by reference in their entireties.

What is claimed is:

1. An antibacterial composition comprising antimicrobial synergistic amounts of a 3-isothiazolone of the following General Formula 1:

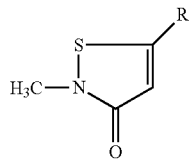

General Formula 1 wherein R is hydrogen or chlorine; and
polyhexamethyleneguanidine phosphate of the following General Formula 2:

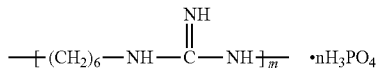

General Formual 2 wherein m is an integer from 4 to 7, n is an integer from 1 to 14, and wherein the weight ratio of 3-isothiazolone to polyhexamethyleneguanidine phosphate has a value of 1:4.

2. The antibacterial composition of claim 1, wherein the 3-isothiazolone is a mixture such that the weight ratio of 3-isothiazolone having R of hydrogen and 3-isothiazolone having R of chlorine has a value in the range of 1:20 to 20:1.

3. The antibacterial composition of claim 1, further comprising a media selected from the group consisting of cooling water for an industrial process, disinfectant, paint, antiseptic for latex, additives for cosmetics, additives for emulsion products, slime control chemicals for textile weaving, paper slime control agent, antiseptic for leather goods, and antiseptic for metal processing oil.

4. A sterilizing method for killing bacteria, the method comprising contacting bacteria with an antibacterial composition, wherein the antibacterial composition comprises antimicrobial synergistic amounts of a 3-isothiazolone of the following General Formula 1:

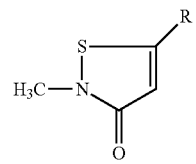

General Formula 1 wherein R is hydrogen or chlorine; and
polyhexamethyleneguanidine phosphate of the following General Formula 2:

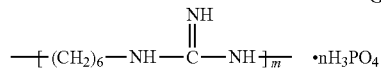

General Formula 2 wherein m is an integer from 4 to 7 and n is an integer from 1 to 14, and wherein the weight ratio of 3-isothiazolone to polyhexamethyleneguanidine phosphate has a value of 1:4.

5. A method for restraining the growth of bacteria, the method comprising contacting bacteria with an antibacterial composition, wherein the antibacterial composition comprises antimicrobial synergistic amounts of a 3-isothiazolone of the following General Formula 1:

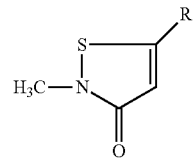

General Formula 1 wherein R is hydrogen or chlorine; and
polyhexamethyleneguanidine phosphate of the following General Formula 2:

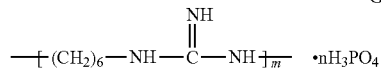

General Formula 2 wherein m is an integer from 4 to 7 and n is an integer from 1 to 14, and wherein the weight ratio of 3-isothiazolone to polyhexamethyleneguanidine phosphate has a value of 1:4.

6. An antifungal composition comprising antimicrobial synergistic amounts of a 3-isothiazolone of the following General Formula 1:

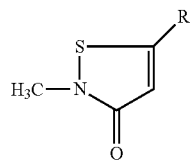

General Formula 1 wherein R is hydrogen or chlorine; and
polyhexamethyleneguanidine phosphate of the following General Formula 2:

General Formula 2 wherein m is an integer from 4 to 7, n is an integer from 1 to 14, and wherein the weight ratio of 3-isothiazolone to polyhexamethyleneguanidine phosphate has a value of 1:4.

7. The antifungal composition of claim 6, wherein the 3-isothiazolone is a mixture such that the weight ratio of 3-isothiazolone having R of hydrogen and 3-isothiazolone having R of chlorine has a value in the range of 1:20 to 20:1.

8. The antifungal composition of claim 6, further comprising a media selected from the group consisting of cooling water for an industrial process, disinfectant, paint, antiseptic for latex, additives for cosmetics, additives for emulsion products, slime control chemicals for textile weaving, paper slime control agent, antiseptic for leather goods, and antiseptic for metal processing oil.

9. A sterilizing method for killing fungi, the method comprising contacting fungi with an antifungal composition, wherein the antifungal composition comprises antimicrobial synergistic amounts of a 3-isothiazolone of the following General Formula 1:

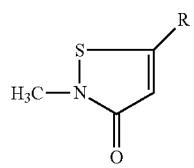

General Formula 1 wherein R is hydrogen or chlorine; and
polyhexamethyleneguanidine phosphate of the following General Formula 2:

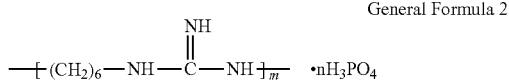

General Formula 2 wherein m is an integer from 4 to 7 and n is an integer from 1 to 14, and wherein the weight ratio of 3-isothiazolone to polyhexamethyleneguanidine phosphate has a value of 1:4.

10. A method for restraining the growth of fungi, the method comprising contacting fungi with an antifungal composition, wherein the antifungal composition comprises antimicrobial synergistic amounts of a 3-isothiazolone of the following General Formula 1:

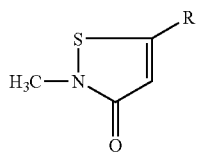

General Formula 1 wherein R is hydrogen or chlorine; and
polyhexamethyleneguanidine phosphate of the following General Formula 2:

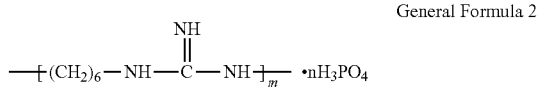

General Formula 2 wherein m is an integer from 4 to 7 and n is an integer from 1 to 14, and wherein the weight ratio of 3-isothiazolone to polyhexamethyleneguanidine phosphate has a value of 1:4.

* * * * *